United States Patent [19]

Wheeler et al.

[11] 4,305,868

[45] Dec. 15, 1981

[54] PHENOLIC ESTERAMIDE ANTIOXIDANTS

[75] Inventors: Edward L. Wheeler, Watertown; Elmar H. Jancis, Naugatuck; Richard A. Gencarelli, Middletown; Franklin H. Barrows, Beacon Falls, all of Conn.

[73] Assignee: Uniroyal, Inc., New York, N.Y.

[21] Appl. No.: 43,771

[22] Filed: May 30, 1979

Related U.S. Application Data

[63] Continuation-in-part of Ser. No. 931,087, Aug. 4, 1978, abandoned.

[51] Int. Cl.$^3$ .......................... C08K 5/37; C08K 5/20; C07C 103/84; C07C 149/36
[52] U.S. Cl. ............................... 260/45.85 B; 560/67; 560/72; 560/75
[58] Field of Search ................... 260/45.85 B; 560/75, 560/67, 72

[56] References Cited

U.S. PATENT DOCUMENTS

| | | | |
|---|---|---|---|
| 3,923,735 | 12/1975 | Schlichting et al. | 260/45.9 NC |
| 4,145,556 | 3/1979 | Hirsch et al. | 260/45.85 B |
| 4,154,723 | 5/1979 | Hirsch et al. | 260/45.85 B |

*Primary Examiner*—V. P. Hoke
*Attorney, Agent, or Firm*—Andrew D. Maslow

[57] ABSTRACT

Novel phenolically substituted esterbisamides as antioxidants useful for the protection of organic materials such as synthetic and natural rubbers, plastics and petroleum products against oxidative degradation.

5 Claims, No Drawings

PHENOLIC ESTERAMIDE ANTIOXIDANTS

BACKGROUND OF THE INVENTION

This application is a continuation-in-part of U.S. Ser. No. 931,087 filed Aug. 4, 1978, now abandoned.

The present invention relates to novel phenolic esteramides which are useful in protecting organic materials such as synthetic and natural rubbers, petroleum products, and plastics from oxidative degradation.

SUMMARY OF THE INVENTION

The present invention relates to compounds of the formula $R^1COOANHCOR^2$ wherein A is $C_2$ to $C_{12}$ alkylene, $C_2$ to $C_5$ alkylene substituted with one or two $—CH_2OCO(CH_2)_mR^3$ groups, wherein $R^3$ is 3-W-5-Y-4-hydroxyphenyl wherein W and Y may be the same or different and are $C_1$ to $C_{12}$ alkyl and m is 0, 1 or 2, or A is $C_4$ to $C_8$ cycloalkylene or $—CH_2—C(CH_2)_p—$ wherein p is an integer from 3 to 6; $R^1$ is $-(CH_2)_m-R^3$ and $R^2$ is $C_1$ to $C_{20}$ alkyl, $C_4$-$C_8$ cycloalkyl, $C_6$ to $C_{10}$ aryl, or phenyl substituted with halogen, $C_1$ to $C_{12}$ alkyl, $C_1$ to $C_{12}$ alkoxy, nitro, or hydroxy, or $R^2$ is BCONHAOCOR' wherein A and $R^1$ are as defined above and B is $C_1$ to $C_{10}$ alkylene, $C_5$ to $C_6$ cycloalkylene, phenylene, $C_4$ to $C_{12}$ thiodialkylene; or when A is a $C_2$ to $C_5$ alkylene substituted with one or two $-(CH_2OCO(CH_2)_mR^3$ groups, $R^2$ is as defined above or is $-(CH_2)_mR^3$ wherein m and $R^3$ are as defined above. The terms alkyl, alkoxy and alkylene comprise linear and branched moieties and the terms cycloalkyl and cycloalkylene include bridged and non-bridged groups. The above description of the invention includes compounds selected from the group consisting of:

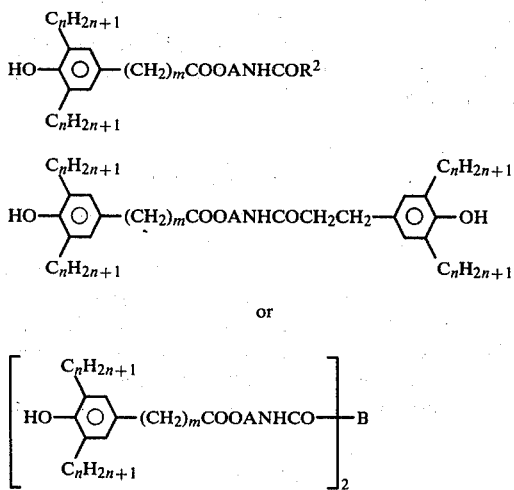

or A is $C_4$ to $C_8$ cycloalkylene or A is $(CH_2)_b—CH—\ominus$ wherein b is 0 or 1 and $\ominus$ represents $C_3$ to $C_6$ cycloalkyl; B is $C_1$ to $C_{10}$ alkylene, phenylene, $C_4$ to $C_{12}$ oxydialkylene or $C_4$ to $C_{12}$ thiodialkylene; $R_2$ is $C_1$ to $C_{12}$ alkyl, $C_6$ to $C_{10}$ aryl, or phenyl substituted with halogen, $C_1$ to $C_{12}$ alkyl, $C_1$ to $C_{12}$ alkoxy, nitro or hydroxy, m has a value of 0, 1 or 2 and n is an integer of from 1 to 12.

The present invention also relates to a process for preparing a compound having the formula $R^1COOANHCOR^2$, wherein A is $C_2$ to $C_{12}$ alkylene, $C_4$ to $C_8$ cycloalkylene, $—CH_2C(CH_2)_p—$ wherein p is an integer from 3 to 6, or A is $C_2$ to $C_5$ alkylene substituted with one or two $—CH_2OCO(CH_2)_mR^3$ groups, wherein $R^3$ is 3-W-5-Y-4-hydroxyphenyl wherein W and Y may be the same or different and are $C_1$ to $C_{12}$ alkyl and m is 0, 1 or 2; $R^1$ is $-(CH_2)_m-R^3$ and $R^2$ may be $-(CH_2)_m R^3$, $C_1$ to $C_{20}$ alkyl, $C_5$ to $C_6$ cycloalkyl, $C_6$ to $C_{10}$ aryl, phenyl substituted with halogen, $C_1$ to $C_{12}$ alkyl, $C_1$ to $C_{12}$ alkoxy, nitro or hydroxy, or $R^2$ is $BCONHACOR^1$, wherein A and $R^1$ are as defined above, and B is $C_1$ to $C_{10}$ alkylene, $C_5$ to $C_6$ cycloalkylene, phenylene, $C_4$ to $C_{12}$ oxydialkylene or $C_4$ to $C_{12}$ thiodialkylene; comprising reacting a compound of the formula $H_2NQ(OH)_s$, wherein s is an integer from 1 to 3 and Q is $C_2$ to $C_{12}$ alkylene, $C_4$ to $C_8$ cycloalkylene, or $—CH_2C(CH_2)_p—$, wherein p is an integer from 3 to 6, with (1) a compound having the formula $R^2COX$ or $B(COX)_2$ wherein $R^2$ and B are as defined above, and X is halogen, hydroxy or $C_1$ to $C_3$ alkoxy, at a temperature of from 15° to 250° C. and a pressure of from 100 Pa to 10 kPa, preferably for 2 to 24 hours, and then the resulting intermediate with (2) a compound having the formula $R^1COX$, wherein $R^1$ and X are as defined above, at a temperature from 15° to 250° C. and a pressure from 100 Pa to 10 kPa, preferably for 2 to 24 hours, provided that if X is halogen, steps (1) and (2) are carried out in the presence of an acid acceptor, and with the further proviso that if $R^1$ and $R^2$ are the same, steps (1) and (2) may be combined. The term halogen as used herein includes fluorine, chlorine, bromine and iodine.

The present invention also relates to a compound of the formula $R^1COOANH_2$ wherein A is $C_2$ to $C_{12}$ alkylene; $C_2$ to $C_5$ alkylene substituted with one or two $—CH_2OCO(CH_2)_mR^3$ groups, wherein $R^3$ is 3-W-5-Y-4-hydroxyphenyl, wherein W and Y may be the same or different and are $C_1$ to $C_{12}$ alkyl and m is 0, 1 or 2; or A is $C_4$ to $C_8$ cycloalkylene or $—CH_2C(CH)_2p—$, wherein p is an integer from 3 to 6; and $R_1$ is a group $—(CH_2)_mR^3$ wherein m and $R^3$ are as defined above.

The present invention also relates to compositions comprising the compounds of the present invention and organic materials subject to oxidative degradation.

A is preferably alkylene having terminal $CH_2—$ groups. Most preferably the ester and amide groups are attached to alpha $CH_2—$ terminated alkylene not having hydrogen on the carbon atoms in the beta-position.

The preferred definition of $R^2$ depends to some extent on the projected use of the product. When high hydrocarbon solubility is desired $R^2$ should be a long chain hydrocarbon having 11 to 17 carbon atoms. In a particularly useful compound $R^2$ is $C_{17}H_{35}$. If low volatility is desired, $R^2$ is preferably $BCONHAOCOR^1$, wherein B, A and $R^1$ are as defined above. Particularly high molecular weights and low volatilities can be achieved when $R^2$ is $BCONHAOCOR^1$ wherein A is an alkylene substituted with $—CH_2OCO(CH_2)_mR^3$ wherein m and $R^3$ are as defined above. The preferred halogens are fluorine, chlorine, bromine and iodine.

The compounds of the present invention are useful in stabilizing organic materials normally subject to oxidative degradation. Materials that are thus stabilized include a multitude of synthetic polymers. Among those polymers are various polyolefins such as polyethylene, polypropylene, polybutylene, polybutadiene, polymethylpentene. Other polymers stabilized by the compounds of the present invention include acetal resins, polyacrylates, polymethacrylates, polydialkylpthalate, cellulosics, polyamides, polyesters, polyurethanes, polycarbonate, polystyrene, polyvinyl chloride, polyvinylidene chloride. Copolymers can also be stabilized by the compounds of the present invention. Representative copolymers include ethylene/propylene copolymers, butadiene/styrene copolymers, ethylene/vinyl acetate copolymers, and ethylene/ethyl acrylate copolymers. Copolymers also include terpolymers such as ethylene/-propylene/non-conjugated diene terpolymers and acrylonitrile/butadiene/styrene interpolymers. Polymer blends such as polystyrene/polyphenylene oxide and ethylenepropylene copolymer or terpolymer/polypropylene can also be stabilized by the compounds of the present invention. Other materials stabilized by compounds of the present invention include hot melt adhesives such as those based on polyesters, polyamides or ethylene/vinyl acetate. Also stabilized are petroleum products such as fuels, lubricating oils, petrolatum jellies, and natural products such as natural rubber, waxes, fat, tallow, linseed oil, corn oil, cottonseed oil, and codliver oil. The preceding list is representative, though by no means exhaustive, of the products that can benefit from the compounds of the present invention. To achieve protection against oxidative degradation, the compounds of the present invention are added in the amounts generally used for known antioxidants which may have similar properties to achieve such protection. Depending on the substrate used, the antioxidant is added in amounts of 0.001 to 10 percent by weight based on the weight of the substrate, with the usual range being from 0.05 to 2.0 percent.

The compounds of the present invention can be used by themselves to stabilize organic materials, or they can be used in combination with other stabilizers. Such other stabilizers might include other phenolics, thio compounds of various kinds, such as thiodipropionate esters, phosphites and phosphonates, anti-copper chemicals such as oxalamides, ultraviolet stabilizers of various kinds as well as other additives where the use of such additives has been found beneficial.

The compounds of the present invention can generally be made from known starting materials by amidification and esterification reactions well known in the literature. Convenient aminoalcohols used in the preparation of the compounds of the present invention include: ethanolamine, 2-aminopropanol, 2-amino-2-methyl-1-propanol, 3-amino-2-methyl-1-propanol, 2-amino-2-methyl-1,3-propanediol, 2-amino-2-ethyl-1,3-propanediol, 2-amino-1-butanol, tris(hydroxymethyl)aminomethane, 1-amino-1-cyclopentanemethanol, 1-aminomethyl-1-cyclohexanemethanol, 6-amino-1-hexanol, 2-amino-3-methyl-1-butanol, 5-amino-1-pentanol, 3-amino-1,2-propanediol, 3-amino-1-propanol, 2-aminocyclohexanol, 4-amino-cyclohexanol, 3-amino-2-butanol, 1-amino-2-dodecanol, 2,2-di-methyl-3-amino-1-propanol, 2-aminomethyl-2-methyl-1,3-propanediol, 2,2,2-tris-(hydroxymethyl)aminoethane. Many other aminoalcohols are readily made by known methods from available starting materials.

A convenient synthesis of a compound of the present invention would generally include making the amide from one of the aforementioned alkanolmines followed by esterification of the hydroxyalkylamide. The amide can readily be prepared by reacting the alkanolamine with an appropriate acid, acid chloride or an ester. Suitable acids include $C_1$ to $C_{21}$ aliphatic acids, benzoic acid, substituted benzoic acids such as alkylbenzoic acid, chlorobenzoic acid, dialkylbenzoic acid, 4-hydroxy-3,5-di-alkyl benzoic acid, 2-(4-hydroxy-3,5-di-alkylphenyl)acetic acid or 3-(4-hydroxy-3,5-di-alkylphenyl)propionic acid.

When the bisamides are desired, then suitable acids include phthalic acid, terephthalic acid, thiodialkanoic acid and aliphatic diacids of the structure HO-CO-$CnH_{2n}$-COOH where n is an integer from 1 to 10. Examples of such acids are malonic, succinic, adipic, palmitic, azaleic, sebacic and others. The esters and acid chlorides of all of the abovementioned acids are likewise suitable starting materials in making amides. It is recognized that imides can form from some of the aforementioned acids. Suitable precautions, such as use of milder conditions and a large excess of amine to maximize amide formation, are advisable in such instances.

The usual starting material for esterification is a 3,5-dialkyl-4-hydroxybenzoic acid, a 2-(3,5-dialkyl-4-hydroxyphenyl) acetic acid or a 3-(3,5-dialkyl-4-hydroxyphenyl)propionic acids, its acid chloride or ester.

If an esteramide is desired where $R^1$ and $R^2$ are identical, the esterification and amidification can be carried out in one step.

The preparations indicated above are mentioned as non-limiting examples of ways to carry out the objects of this invention. Other methods will suggest themselves to those skilled in the art.

The following non-limiting examples further illustrate the preparation and use of the compounds of the present invention.

EXAMPLE 1

N-(2-hydroxyethyl)lauramide

To a solution of 24 g (0.4 mole) ethanolamine in 100 ml toluene was added 40 g (0.2) lauric acid at 50° C. The mixture was refluxed for 6 hours. Toluene was gradually removed to increase the final pot temperature to 140° C. The distillate was collected in a Stark & Dean trap. The toluene was removed by vacuum stripping and the residue was crystallized from n-hexane. The title compound (44 g) thus obtained melted at 80°–84° C.

EXAMPLE 2

2-(lauramido)ethyl 3-(3,5-di-tert-butyl-4-hydroxyphenyl)-propionate

A mixture of 13.9 g (0.055 mole) N-(2-hydroxyethyl)-lauramide, 13.9 g (0.05 mole) 3(3,5-di-tert-butyl-4-hydroxyphenyl)propionic acid, 0.5 g Tyzor TBT catalyst and 100 ml xylene was refluxed until evolution of water ceased (3 hours). The xylene was removed by vacuum stripping. The residue was taken up in acetonitrile. White crystals separated upon cooling at about −10° C. The acetonitrile was decanted and the recrystallization was repeated. The last traces of acetonitrile were removed under vacuum, and the title product thus obtained was a yellow oil at room temperature.

EXAMPLE 3

N-(2-hydroxyethyl)stearamide

To a solution of 24.4 g (0.4 mole) ethanolamine in 500 ml ethanol at 60° C. was added 85.2 g (0.3 mole) stearic acid. The ethanol was distilled off until the pot temperature reached 100° C., at which time 300 ml toluene was added, and the water was distilled off as an azeotrope. After 5 hours at 110° C., 6 ml water was recovered in the Stark & Dean trap. Some toluene was removed to raise the pot temperature to 135° C. After an additional 4 hours, another 7 ml water was trapped. The title product (38.5 g) that crystallized on cooling had a melting point of 96°–99° C.

EXAMPLE 4

2-stearamidoethyl 3-(3,5-di-tert-butyl-4-hydroxyphenyl)propionate

A mixture of 30.6 g (0.11 mole) 3-(3,5-di-tert-butyl-4-hydroxyphenyl)propionic acid, 32.6 g (0.1 mole) N-(2-hydroxyethyl)stearamide, 0.8 g Tyzor TBT, and 100 ml xylene was refluxed for six hours. The water (1.8 ml) was trapped in a Stark & Dean trap. The solution was filtered through Microcel (trademark, synthetic calcium silicate) and the solvent was removed by vacuum stripping. The title compound (51 g) was recrystallized from acrylonitrile. It melted at 52°–55° C.

EXAMPLE 5

2-[3-(3,5-di-tert-butyl-4-hydroxyphenyl)propionamido]ethyl 3-(3,5-di-tert-butyl-4-hydroxyphenyl)propionate A mixture of 32 g (0.1 mole) of 3-(3,5-di-tert-butyl-4-hydroxyphenyl)-N-(2-hydroxyethyl)propionamide, 27 g (0.1 mole) of 3(3,5-di-tert-butyl-4-hydroxyphenyl)propionic acid, 1 g Tyzor TBT catalyst and 100 ml xylene was refluxed at 150° until evolution of water ceased. In the course of four hours, two ml water was collected in the Stark & Dean trap. The xylene was removed by vacuum stripping. The title compound (54 g) was recrystallized from a toluene/hexane mixture. It melted at 151°–154° C.

EXAMPLE 6

2-amino-2-methylpropyl [3-(3,5-di-tert-butyl-4-hydroxyphenyl)propionate]

In a 1-liter, three-neck, round-bottom flask equipped with a thermometer, stirrer and condenser were placed 66.2 g (0.2 mole) 2-[2-(3,5-di-tert-butyl-4-hydroxyphenyl)ethyl]-4,4-dimethyl-2-oxazoline, prepared as disclosed in inventors' application Ser. No. 043,787, filed on May 30, 1979, now abandoned and application Ser. No. 181,325, filed on Aug. 25, 1980 which is a continuation of said application Ser. No. 043,787, entitled "Derivatives of 2-Oxazolines as antioxidants," assigned to Uniroyal, Inc. and filed concurrently herewith, the disclosure of which is hereby incorporated herein by reference, 400 ml isopropanol and 33 ml 6 N hydrochloric acid. The mixture was heated to 45° C. for 2 hours and then cooled. To this stirred solution were added 250 ml of water and 33 ml of 6 N sodium hydroxide. The product was removed by filtration and dried. The title compound, (52 g), thus obtained, melted at 97°–99° C.

EXAMPLE 7

2-palmitamido-2-methylpropyl-3-(3,5-di-tert.-butyl-4-hydroxyphenyl)propionate In a 1-liter, three-neck, round-bottom flask equipped with a thermometer, stirrer and dropping funnel were placed 17.5 g (0.05 mole) of 2-amino-2-methylpropyl 3-(3,5-di-t-butyl-4-hydroxyphenyl)propionate, 500 ml of benzene and 10 g of triethylamine. To this stirred mixture was added 14 g (0.05 moles) of palmitoyl chloride and the mixture stirred for four hours. The mixture was filtered and stripped, and the residue dissolved in hot acetonitrile. After being stored for about 4 days at about 5° C., the product crystallized. it was removed by filtration and dried. The title compound, (14 g) thus obtained, melted at 43°–46° C.

EXAMPLE 8

2-stearamido-2-methylpropyl 3-(3,5-di-tert-butyl-4-hydroxyphenyl)propionate

In a 500 ml, three-neck, round-bottom flask equipped with a thermometer, stirrer and dropping funnel were placed 26 g (0.75 mole) of 2-amino-2-methylpropyl 3-(3,5-di-t-butyl-4-hydroxyphenyl)propionate, 200 ml of benzene and 8.2 g of triethylamine. To this stirred mixture was added 22.5 g (0.075 mole) of stearoyl chloride, and the mixture stirred for 4 hours. The triethylamine hydrochloride was removed by filtration and the solvent was stripped off. The residue was dissolved in hot hexane. After crystallization, filtration and drying, the title compound melted at 46°–48° C.

EXAMPLE 9

2-[3-(3,5-di-tert-butyl-4-hydroxyphenyl)propionamido]isobutanetriyl tris[3-(3,5-di-tert-butyl-4-hydroxphenyl)-propionate]

A solution of 85 g (0.27 mole) 3(3,5-di-tert-butyl-4-hydroxyphenyl)propionyl chloride in 120 ml toluene was added to 7.3 g (0.06 mole) tris(hydroxymethyl)aminomethane in 60 ml pyridine and 30 ml toluene. The mixture was stirred 42 hours at 60° C. The mixture was washed with dilute acid and then with brine. The toluene was removed by vacuum stripping and the residue was crystallized in n-hexane. The title compound thus obtained melted at 118°–122° C.

| Elemental Analyses: | Calculated | Found |
|---|---|---|
| C | 74.37 | 74.19 |
| H | 9.28 | 9.47 |
| N | 1.21 | 1.11 |

EXAMPLE 10

2-stearamidoisobutanetriyl tris[3-(3,5-dl-tert-butyl-4-hydroxyphenyl)propionate]

To 44.2 g (0.05 mole) of 2-[3-(3,5-di-tert-butyl-4-hydroxyphenyl)ethyl]-2-oxazoline-4,4-dimethyl bis[3-(3,5-di-tert.-butyl-4-hydroxyphenyl)propionate], prepared as disclosed in the inventors' application Ser. No. 043,787, filed on May 30, 1979, now abandoned and application Ser. No. 181,325, filed on Aug. 25, 1980 which is a continuation of said application Ser. No. 043,787, entitled "Derivatives of 2-Oxazolines as Antioxidants", assigned to Uniroyal, Inc. and filed on even date herewith, the disclosure of which is hereby incorporated herein by reference, in 200 ml toluene was added 8.2 ml 6 N hydrochloric acid. The mixture was stirred for 4 hours, and 8 g sodium bicarbonate was then added. The water layer was separated, and to the organic layer was added 40 ml triethylamine, followed by 15.1 g (0.05 mole) stearoyl chloride in 30 ml toluene. This mixture was stirred overnight at room temperature and was then stirred one hour at 50° C. Upon cooling, the mixture was washed first with dilute hydrochloric acid and then with brine. The toluene was removed by vacuum stripping. The residue was purified by passing it through a silica column using 50/50 (volume) toluene/hexane mixture as the eluent. The title compound (28 g) obtained after evaporation of the eluent, melted at 77°–79° C.

EXAMPLE 11

2,2'-adipamidobis-[2-methylpropyl 3-(3,5-di-tert-butyl-4-hydroxyphenyl)propionate]

In a 1-liter, three-neck, round-bottom flask equipped with a thermometer, stirrer and dropping funnel were placed 29 g (0.083 mole) of 2-amino-2-methylpropyl [3-(3,5-di-t-butyl-4-hydroxyphenyl)propionate], 20 g of triethylamine and 400 ml benzene. To this stirred mixture was added 7.6 g (0.0415 mole) of adipoyl chloride, and the mixture was stirred for 4 hours. The mixture was filtered and stripped, and the residue dissolved in hot hexane. The product crystallized and was then recrystallized from a mixture of 400 ml of isooctane-125 ml of toluene. The purified product (21 g) melted at 135°–138° C.

EXAMPLE 12

2,2'-sebacamidobis-[2-methylpropyl 3-(3,5-di-tert-butyl-4-hydroxyphenyl)propionate]

In a 1-liter, three-neck, round-bottom flask equipped with a thermometer, stirrer and dropping funnel were placed 34.9 g (0.1 mole) of 2-amino-2-methylpropyl 3-(3,5-di-t-butyl-4-hydroxyphenyl)propionate, 20 g of triethylamine and 400 ml of benzene. To this stirred mixture was added 11.9 g (0.05 mole) of sebacoyl chloride, and the mixture was stirred for 5 hours. The mixture was filtered and stripped, and the residue was dissolved in hot hexane. A solid separated and it was recrystallized from hexane/benzene (3:1). The title compound (32 g) thus obtained melted at 113°–117° C.

EXAMPLE 13

2,2'-sebacamidobis[isobutanetriyl tris[3-(3,5-di-tert-butyl-4-hydroxyphenyl)propionate]]

To 44.2 g (0.05 mole) of 2-[2-(3,5-di-tert-butyl-4-hydroxyphenyl)ethyl]-2-oxazoline-4,4-dimethyl bis[3-(3,5-di-tert-butyl-4-hydroxyphenyl)propionate] in 200 ml toluene was added 8.2 ml 6 N hydrochloric acid. The mixture was stirred for 3 hours, and 6 g sodium bicarbonate was then added. The mixture was stirred 15 minutes, and the layers were separated. To the organic layer was added 40 ml triethylamine followed by 6 g (0.025 mole) sebacoyl chloride in 30 ml toluene. This mixture was stirred overnight at room temperature, and was then stirred one hour at 50° C. Upon cooling, the mixture was washed first with dilute hydrochloric acid and then with brine. The toluene was removed by vacuum stripping. The residue was taken up in 1:1 toluene/hexane and passed through a fluorosil column. The title compound (11 g), isolated after removal of solvent, melted at 134°–141° C.

EXAMPLE 14

N,N'-bis[1,1-bis(hydroxymethyl)-2-hydroxyethyl]-terephthalamide

In a 1-liter, three-neck, round-bottom flask equipped with a thermometer, stirrer and condenser were placed 194 g (1.0 mole) of dimethyl terephthalate, 242 g (2.0 mole) tris(hydroxymethyl) aminomethane and 1 liter of methanol. The mixture was refluxed for 8 hours and then allowed to cool. The title compound crystallized and was removed by filtration and dried. The melting point was 188°–190° C.

EXAMPLE 15

2,2'-terephthalamidobis[isobutanetriyl tris[3-(3,5-di-tert-butyl-4-hydroxyphenyl)propionate]]

In a 1-liter, three-neck, round-bottom flask equipped with a thermometer, stirrer, dropping funnel and condenser were placed 18.6 g (0.05 mole) of N,N'-bis[1,1-bis(hydroxymethyl)-2-hydroxyethyl]terephthalamide and 200 ml of pyridine. To this stirred slurry was added 90 g (0.3 mole) of 3-(3,5-di-t-butyl-4-hydroxyphenyl)-propionyl chloride at 20°–30° C., and the mixture was stirred for 18 hours. The mixture was filtered and stripped, and the residue was dissolved in hot cyclohexane. Trace amounts of pyridine hydrochloride were filtered off and the solution was allowed to cool. The title product (61 g) crystallized on cooling. After recrystallization from methanol, it melted at 169°–172° C.

EXAMPLE 16

3,3'-Thiobis[2-propionamidoethyl-3-di-tert-butyl-4-hyphenyl)propionate]

A solution of 26.8 g (0.44 mole) ethanolamine and 41.2 g (0.2 mole) dimethyl 3,3'-thiodipropionate in 100 ml ethanol was refluxed for 5 hours. The 3,3'-thiobis-[N-(2-hydroxyethyl)propionamide] precipitated as a white crystalline solid and upon washing with acetone melted at 130°–132°.

A mixture of 18 g (0.068 mole) at the aforementioned intermediate, 41.7 g (0.15 mole) 3-(3,5-di-tert-butyl-4-hydroxyphenyl)propionic acid and 1 g Tyzor TBT catalyst in 100 ml xylene was refluxed until evolution of water ceased. 3.5 ml of water was recovered in the Stark and Dean trap. Upon evaporation of the xylene, the product (51 g) was obtained as a viscous yellow oil.

EXAMPLE 17

3,3'-thiobis[2-methyl-2-propionamidopropyl-3-(3,5-di-tert-butyl-4-hydroxyphenyl)propionate]

A mixture of 40 g (0.44 mole) 2-amino-2-methylpropanol, 3 g of potassium tert-butoxide and 41.2 g (0.2 mole) dimethyl 3,3'-thiodipropionate was stirred for ½ hour at room temperature and was then heated to 90° C. for ½ hour under vacuum. The excess 2-amino-2-methylpropanol was removed by vacuum stripping. One-half (0.1 mole) of the resulting 3,3'-thiobis-N-(1,1-dimethyl-2-hydroxyethyl)propionamide was heated with 61.2 g (0.2 mole) ethyl 3-(3,5-di-tert-butyl-4-hydroxyphenyl) propionate and 2 g potassium tert-butoxide for 2 hours under vacuum at 100°–110° C. The mixture was taken up in toluene, neutralized with acetic acid and washed with water. Upon removal of the toluene by vacuum distillation, the title compound (79 g) was obtained as a viscous yellow oil.

EXAMPLE 18

N,N'-bis[2-hydroxyethyl]terephthalamide

A mixture of 194 g (1.0 mole) of dimethyl terephthalate, 150 ml (2.46 mole) ethanolamine and 300 ml ethanol was refluxed for 7 hours. On cooling the title product separated. It was filtered and then washed with ethanol. After drying, it melted at 227°–229° C.

EXAMPLE 19

2,2'-terephthalamido-N,N'-bis[ethyl[3-(3,5-di-tert-butyl-4-hydroxyphenyl)propionate]]

To a mixture of 25.2 g (0.1 mole) N,N'-bis(2-hydroxyethyl)terephthalamide and 200 ml pyridine was added 59.3 g (0.2 mole) of 3-(3,5-di-tert-butyl-4-hydroxyphenyl)propionyl chloride in 300 ml toluene. The mixture was stirred for 2 hours. It was then heated to 90° C. and filtered hot. The solvent was removed by distillation and the residue was crystallized from n-hexane. The title product (68 g) thus obtained was filtered and then washed with hot water. After drying, it melted at 173°–175° C.

EXAMPLE 20

3-stearamidopropyl 3(3,5-di-tert-butyl-4-hydroxyphenyl)propionate

Stearic acid (56.8 g; 0.2 mole) was added to a hot (80° C.) mixture of 30 g (0.4 mole) 3-aminopropanol, 100 ml xylene and 0.5 g sodium methoxide. The mixture was heated at reflux for two hours with removal of water and was then poured into hexane, in which N-(3-hydroxypropyl)stearamide crystallized and was obtained by filtration; it melted at 83°–89° C. After the product was recrystallized from acetone, melting point rose to 94°–96° C. A 34.1 g (0.1 mole) portion of this intermediate was heated with 27.8 g (0.1 mole) of 3-(3,5-di-tert-butyl-4-hydroxyphenyl)propionic acid, 1 g of Tyzor TBT catalyst and 100 ml xylene. After the mixture was refluxed for 3 hours, 2 ml of water was collected in the Stark and Dean trap. The xylene was distilled off under vacuum, and the residue was crystallized from acetonitrile. The title product (29 g) thus obtained melted at 50°–52° C.

EXAMPLE 21

N-(2,2-dimethyl-3-hydroxypropyl) stearamide

In a 500 ml, three-neck, round-bottom flask equipped with a thermometer, stirrer and a Stark and Dean trap with condenser were placed 119.4 g of methyl stearate, 41 g of 3-amino-2,2-dimethylpropanol and 3 g of potassium tert-butoxide. The mixture was heated to 190° C., and the methanol distilled off. The reaction mixture was dissolved in hot isopropanol and filtered. On cooling, the product crystallized, and after filtration and drying it melted at 44° C. IR showed an ester carbonyl. The pure product was obtained by washing with hot hexane. The pure product melted at 68°–69° C.

EXAMPLE 22

2,2-Dimethyl-3-stearamidopropyl 3-(3,5-di-tert-butyl-4-hydroxylphenyl)propionate In a 1-liter three-neck, round-bottom flask equipped with a thermometer, stirrer, dropping funnel and condenser were placed 36.9 g of N-(2,2-dimethyl-3-hydroxypropyl)-stearamide, 25 ml of triethylamine and 250 ml of toluene. To this stirred mixture was added 29.6 g of 3-(3,5-di-tert-butyl-4-hydroxyphenyl)propionyl chloride. The mixture was filtered, stripped, and the residue was dissolved in hot methanol. The 2,2-dimethyl-3-stearamidopropyl stearate, melting at 60°–62° C. was isolated. The methanol solution was stripped, and the residue was dissolved in acetonitrile. The title compound was isolated; it melted at 44° C.

EXAMPLE 23

2-Stearamidoethyl 3,4-di-tert-butyl-4-hydroxybenzoate

A mixture of 25 g (0.1 mole) 3,5-di-tert-butyl-4-hydroxybenzoic acid, 50 ml toluene and 8.5 ml thionyl chloride was refluxed for 3 hours. The excess thionyl chloride and the toluene were removed on a rotary evaporator. The acid chloride was dissolved in 50 ml toluene and was added to a mixture of 29.4 g (0.09 mole) N-(2-hydroxyethyl)stearamide, 20 ml toluene and 15 ml pyridine. The mixture was refluxed for two hours. The reaction mixture was then cooled, quenched with water, washed with dilute hydrochloric acid and with water. The toluene was removed by distillation, and the residue was crystallized from hexane. The title compound thus obtained melted at 56°–58° C.

EXAMPLE 24

This example shows the usefulness of the compounds of the present invention in polypropylene. It also shows the beneficial effect observed by using the compounds of the present invention in conjunction with a co-stabilizer. The particular compound used in each run of this Example and of the succeeding Examples is identified by the number of one of the above Examples in which the preparation of the compound is described.

The stabilizers were incorporated into Profax 6501 (trademark) polypropylene resin on a mill at 166° C. Seventy-five mil plaques (discs approximately one inch in diameter and 75 mil (1.9 mm) thick) were prepared by compression molding in a press at 27,000 psi (186 MPa) and 177° C. These specimens were placed in a forced air oven at 149° C., and the number of days required for embrittlement to occur was noted. When two out of three buttons embrittled (that is, they become granular due to heat aging), the specimen was considered to have failed. The results are shown in Table I.

TABLE 1

| Compound/Co-Stabilizer | Concentration* | Days to Failure |
|---|---|---|
| none | — | 1 |
| DSTDP | 0.2 | 4 |
| Example 4 | 0.2 | 32 |
| Example 4/DSTDP | 0.1/0.1 | 25 |
| Example 6 | 0.2 | 34 |
| Example 6/DSTDP | 0.1/0.1 | 61 |
| Example 7 | 0.2 | 39 |
| Example 7/DSTDP | 0.1/0.1 | 60 |
| Example 9 | 0.2 | 43 |
| Example 9/DSTDP | 0.1/0.1 | 69 |
| Example 10 | 0.2 | 48 |
| Example 10/DSTDP | 0.1/0.1 | 78 |
| Example 11 | 0.2 | 28 |
| Example 11/DSTDP | 0.1/0.1 | 45 |
| Example 12 | 0.2 | 35 |
| Example 12/DSTDP | 0.1/0.1 | 48 |
| Example 13 | 0.2 | 55 |
| Example 13/DSTDP | 0.1/0.1 | 76 |
| Example 15 | 0.2 | 61 |
| Example 15/DSTDP | 0.1/0.1 | 55 |
| Example 19 | .2 | 40 |

TABLE 1-continued

| Compound/Co-Stabilizer | Concentration* | Days to Failure |
|---|---|---|
| Example 19/DSTDP | 0.1/0.1 | 64 |

*parts by weight per hundred parts by weight of polypropylene
**distearyl thiodipropionate

EXAMPLE 25

This example shows the usefulness of the compounds of the present invention in EPDM (ethylene/propylene/5-ethylidene-2-norbornene terpolymer having an ethylene/propylene weight ratio of 67/33, an iodine number of 10 and a Mooney viscosity (ML-4 at 120° C.) of 57).

The stabilizers (0.165 g) were dissolved in a rubber cement containing 110 g of EPDM in 2,000 g hexane. The hexane was removed by slowly adding the cement to boiling water. The solids were removed from the boiling water by filtration and were dried on a mill for 5 minutes at 275°–300° F. (135°–149° C.).

The time necessary for a 1 g sample to absorb 20 cm of oxygen at 150° C. was then determined ($T_{20}$). The results are shown in Table 2, indicating the excellent protection conveyed on the EPDM through the presence of the compounds of the present invention.

TABLE 2

| Additive | $T_{20}$ (minutes) |
|---|---|
| None | 30 |
| Example 8 | 260 |

EXAMPLE 26

This example shows the usefulness of the compounds of the present invention in high impact polystyrene.

The antioxidant (0.25 parts by weight per hundred parts by weight of polystyrene) was milled into a high impact polystyrene stock at 138° C. Notched Izod bars were molded at 170° C. After a determination of impact strength was made, the Izod bars were ground and remolded. This procedure was repeated five times. The percent impact strength retention after five moldings is shown below in Table 4.

TABLE 4

| Antioxidant | % Impact Strength Retention |
|---|---|
| None | 58.3 |
| Example 8 | 66.3 |

We claim:

1. A phenolic esteramide selected from the group consisting of:

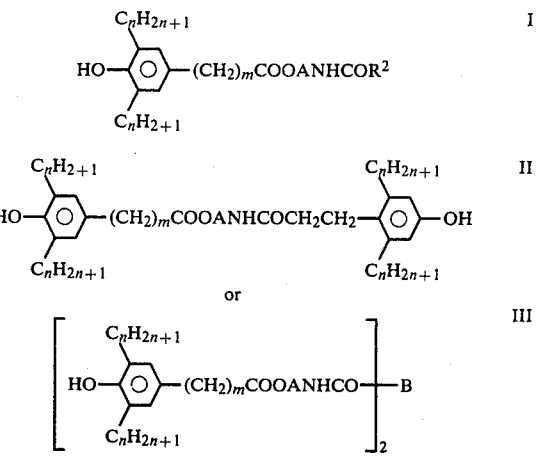

or

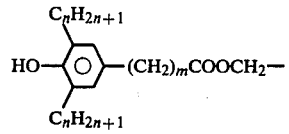

wherein A is $C_2$ to $C_{12}$ alkylene or $C_2$ to $C_5$ alkylene substituted with one or two groups having the formula (aa):

$$HO-\underset{C_nH_{2n+1}}{\overset{C_nH_{2n+1}}{\text{C}_6H_3}}-(CH_2)_mCOOCH_2-$$

or A is $C_4$ to $C_8$ cycloalkylene or A is $(CH_2)_b$—CH— O wherein b is 0 or 1 and O represents $C_3$ to $C_6$ cycloalkyl; B is $C_1$ to $C_{10}$ alkylene, phenylene, $C_4$ to $C_{12}$ oxydialkylene or $C_4$ to $C_{12}$ thiodialkylene; $R_2$ is $C_1$ to $C_{12}$ alkyl, $C_6$ to $C_{10}$ aryl, or phenyl substituted with halogen, $C_1$ to $C_{12}$ alkyl, $C_1$ to $C_{12}$ alkoxy, nitro or hydroxy, m has a value of 0, 1 or 2 and n is an integer from 1 to 12.

2. The compound of claim 1 wherein A is $C_2$ to $C_5$ alkylene, or $C_2$ to $C_5$ alkylene substituted by at least one group of formula (aa), the $C_nH_{2n+1}$ moiety is a secondary or tertiary alkyl wherein n is an integer from 3 to 8; and $R^2$ is $C_{11}$ to $C_{17}$ alkyl.

3. The compound of claim 2 wherein $C_nH_{2n+1}$ is tertiary alkyl, and n is a 4.

4. The compound of claim 1 wherin B is phenylene, thiodiethylene or $C_4$ to $C_8$ alkylene; and m is 2.

5. A composition comprising an organic material subject to oxidative degradation and an effective amount of a compound of claim 1 to inhibit such degradation.

* * * * *